United States Patent [19]

Varma

[11] 4,447,363
[45] * May 8, 1984

[54] ANDROSTENE-17-DITHIOKETALS

[75] Inventor: Ravi K. Varma, Belle Mead, N.J.

[73] Assignee: E. R. Squibb & Sons, Inc., Princeton, N.J.

[*] Notice: The portion of the term of this patent subsequent to Nov. 30, 1999 has been disclaimed.

[21] Appl. No.: 396,178

[22] Filed: Jul. 7, 1982

[51] Int. Cl.³ ............................................... C07J 1/00
[52] U.S. Cl. .............................. 260/397.3; 260/397.45
[58] Field of Search ......................... 260/397.3, 397.45

[56] References Cited

U.S. PATENT DOCUMENTS 4,361,559 11/1982 Varma .............................. 260/397.3

Primary Examiner—Elbert L. Roberts
Attorney, Agent, or Firm—Lawrence S. Levinson; Donald J. Barrack

[57] ABSTRACT

Antiinflammatory activity is exhibited by steroids having the formula

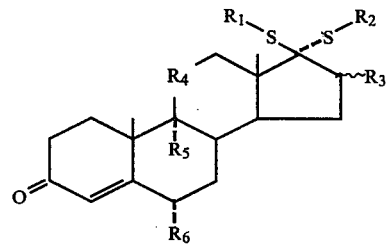

and the 1,2-dehydro, 6,7-dehydro and 15,16-dehydro derivatives thereof, wherein one of $R_1$ and $R_2$ is alkyl, cycloalkyl, aryl, arylalkyl, or —$CH_2X$ wherein X is alkylthio, alkoxy, aroyloxy, alkanoyloxy or alkoxycarbonyl, and the other is alkylthioalkyl, alkoxyalkyl, alkanoyloxyalkyl, aroyloxyalkyl, alkoxycarbonylalkyl, carboxyalkyl or arylalkyl;

$R_3$ is hydrogen, hydroxy, alkoxy, aryloxy, oxo, methylene, alkylthio, arylthio, alkanoyl, alkanoyloxy, or halogen;

$R_4$ is carbonyl or $\beta$-hydroxymethylene;

$R_5$ is hydrogen or halogen; and $R_6$ is hydrogen, methyl, hydroxy, alkanoyl or halogen.

16 Claims, No Drawings

ANDROSTENE-17-DITHIOKETALS

RELATED APPLICATION

U.S. patent application Ser. No. 294,680, filed Aug. 20, 1981, now U.S. Pat. No. 4,361,559, issued Nov. 30, 1982, discloses 17,17-bis-(substituted thio)androstenes having the partial structural formula

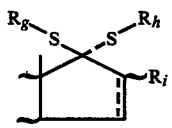

wherein $R_g$ and $R_h$ are the same or different and each is alkyl, cycloalkyl, or aryl; $R_i$ is hydrogen, hydroxy, alkoxy, aryloxy, alkylthio, arylthio,

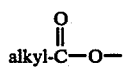

or halogen; and the broken line in the 15,16-position represents the optional presence of ethylenic unsaturation. The steroids have antiinflammatory activity.

BACKGROUND OF THE INVENTION

U.S. Pat. Nos. 4,091,036, issued May 23, 1978, 4,094,840, issued June 13, 1978, 4,133,811, issued Jan. 9, 1979, and 4,146,538, issued Mar. 27, 1979, each discloses androstenes intermediates having the partial structural formula

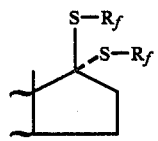

wherein $R_f$ is alkyl or aryl, and both $R_f$ groups are the same.

BRIEF DESCRIPTION OF THE INVENTION

Steroids having the formula

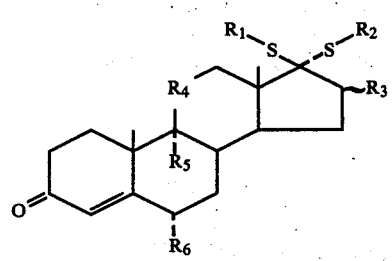

and the 1,2-dehydro, 6,7-dehydro and 15,16-dehydro derivatives thereof, have topical antiinflammatory activity. In formula I, and throughout the specification, the symbols are as defined below.

One of $R_1$ and $R_2$ is alkyl, cycloalkyl, aryl, arylalkyl, or —$CH_2X$ wherein X is alkylthio, alkoxy, aroyloxy, alkanoyloxy or alkoxycarbonyl, and the other is alkylthioalkyl, alkoxyalkyl, alkanoyloxyalkyl, aroyloxyalkyl, alkoxycarbonylalkyl, carboxyalkyl or arylalkyl;

$R_3$ is hydrogen, hydroxy, alkoxy, aryloxy, oxo (=O), methylene (=$CH_2$), alkylthio, arylthio, alkanoyl, alkanoyloxy, or halogen;

$R_4$ is carbonyl or β-hydroxymethylene;

$R_5$ is hydrogen or halogen; and $R_6$ is hydrogen, methyl, hydroxy, alkanoyl or halogen.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The term "cycloalkyl", as used throughout the specification, either individually or as part of a larger group, refers to groups having 3,4,5,6 or 7 carbon atoms.

The term "alkanoyl", as used throughout the specification either individually or as part of a larger group, refers to groups having 2 to 13 carbon atoms.

The term "aroyloxy" as used throughout the specification either individually or as part of a larger group, refers to groups having the formula

DETAILED DESCRIPTION OF THE INVENTION

The steroids of formula I, and the 1,2-dehydro, 6,7-dehydro and 15,16-dehydro derivatives thereof, are topical antiinflammatory agents that can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. U.S. Pat. Nos. 3,948,264 and 4,147,166 and exemplary of the literature which describes devices that can be used to administer solid medicaments for inhalation therapy.

The steroids of formula I, and the 1,2-dehydro, 6,7-dehydro and 15,16-dehydro derivatives thereof, can be prepared utilizing androstenes having the formula

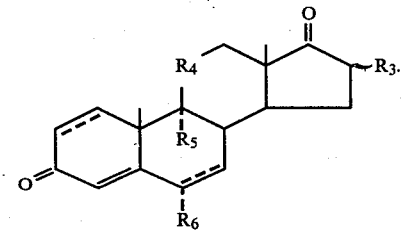

In formula II, and throughout the specification, a broken line in the steroid rings indicates the optional presence of ethylenic unsaturation.

Reaction of an androstene of formula II with a thiol having the formula $R_1$—SH,                         III in the presence of a Lewis acid (e.g., boron trifluoride etherate) yields a steroid having the formula

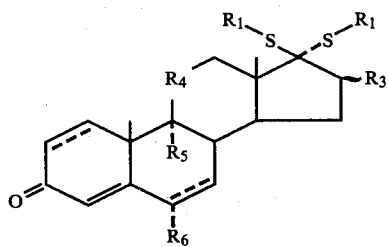

The reaction can be run in an organic solvent (e.g., a halogenated hydrocarbon), or a mixture of organic solvents. The use of glacial acetic acid as the sole solvent, or in admixture with other solvents, improves yields. Reaction conditions are not critical and the reaction can be conveniently run at room temperature, preferably in an inert atmosphere, (e.g., argon or nitrogen). Better yields can be obtained with relatively short reaction times (less than 1 hour). The addition of a dimethylformamide dialkyl acetal (preferably dimethylformamide dimethyl acetal) also improves yields.

To prepare the steroids of formula I wherein $R_1$ and $R_2$ are different, an androstene of formula IV is first converted to the corresponding androstene having the formula

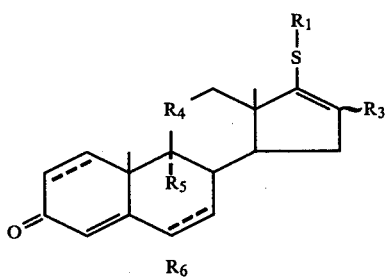

by simply heating the steroid, either neat or in an inert solvent (e.g., diethylbenzene or dichlorobenzene). Alternatively, steroids of formula IV can be oxidized with a peracid (e.g., m-chloroperbenzoic acid) at low temperature (from about −78° C. to 0° C.) and the resulting monosulfoxide heated in an inert solvent to give an androstene of formula V.

Alternatively, compounds of formula V, wherein $R_3$ is chlorine, bromine, alkylthio, or arylthio can be prepared from the corresponding steroid of formula V wherein $R_3$ is hydrogen; i.e., a steroid having the formula

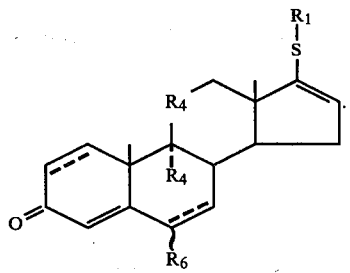

Utilizing the procedure described in U.S. Pat. No. 4,265,815, issued May 5, 1981, a steroid of formula V wherein $R_3$ is chlorine or bromine can be obtained by reacting a steroid of formula VI with the appropriate N-halosuccinimide, or with chlorine or bromine, preferably in a halogentated hydrocarbon solvent. Steroids of formula V wherein $R_3$ is alkylthio or arylthio can be obtained by reacting the corresponding steroid of formula VI with an alkyl or aryl sulfenyl halide, preferably in a halogenated hydrocarbon solvent.

Reaction of a steroid of formula V with a thiol having the formula $R_2$—SH                         VII yields the corresponding steroid having the formula

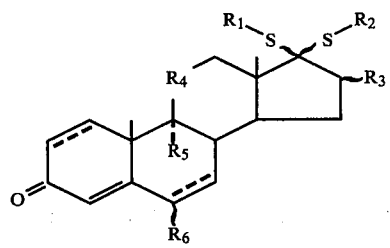

as a mixture of isomers. The reaction is run in the presence of a Lewis acid (e.g., boron trifluoride etherate) and will preferably be run at a reduced temperature (i.e., about −20° C. to −100° C.). When the reaction is run at a reduced temperature (i.e., about −20° C. to −100° C.), it is stereospecific, and yields a steroid having the formula

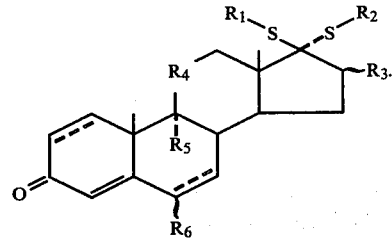

The 11-hydroxyl group of a steroid of formula V may be protected before its reaction with a thiol of formula VII. An exemplary family of protecting groups is the acyl family, e.g., alkanoyl groups such as acetyl. Means for protection and deprotection of the 11-hydroxyl group are well-known in the art. When preparing a compound of formula VIII or IX from an androstene-3,17-dione of formula II, it may be desirable to protect the 11-hydroxyl group as the first step of the synthesis.

When a steroid of formula V wherein $R_1$ is alkanoyloxymethyl is reacted with a thiol of formula VII wherein $R_2$ is alkyl, a desirable side product is obtained in addition to the steroid of formula VIII; i.e., a steroid having the formula

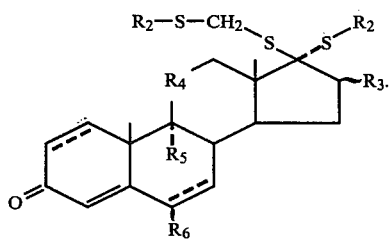 X

The steroids of formula I having ethylenic unsaturation in the 15,16-position can be prepared from the corresponding 16-haloandrostene. Refluxing the 16-haloandrostene is an organic solvent in the presence of 1,5-diazabicyclo (5.4.0) undec-5-ene yields the desired 15,16-unsaturation. Alternatively, the steroids of formula I having ethylenic unsaturation in the 15,16-position can be prepared from the corresponding 16-hydroxyandrostene. Dehydrating the 16-hydroxyandrostene, using a dehydrating agent such as thionyl chloride or phosphorus oxychloride yields the desired 15,16-unsaturation.

The starting androstenes of formula II can be prepared by treating the corresponding pregnene having the formula

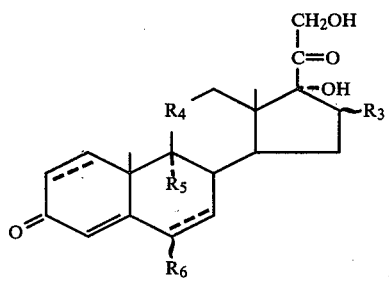 XI with sodium bismuthate in the presence of an acid, such as acetic acid.

Alternatively, the starting androstenes of formula II wherein $R_3$ is hydroxy or

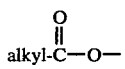
alkyl-C—O— can be prepared by oxidation of the corresponding androstene having the formula

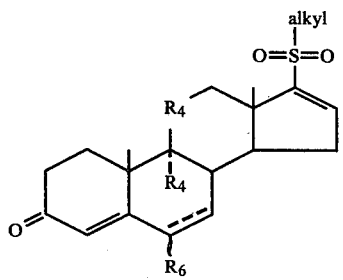 XII with potassium permanganate in the presence of formic acid. The oxidation reaction yields the corresponding 16α(and 16β)-hydroxyandrostene-3,17-dione. These can be acylated using art-recognized procedures to yield the corresponding 16-alkanoyloxy derivative.

The following examples are specific embodiments of this invention.

EXAMPLE 1

(11β)-17-[[(Acetyloxy)methyl]thiol]-17-(ethylthio)-9-fluoro-11-hydroxypregna-1,4-dien-3-one (isomer A) and
(11β)-17-(ethylthio)-17-[[(ethylthio)methyl]thio]-9-fluoro-hydroxyandrosta-1,4-dien-3-one (isomer A)

A solution of 1.5 g (3.69 mmole) of 17-[[(acetyloxy)methyl]thio]-9-fluoro-11β-hydroxyandrosta-1,4,16-trien-3-one, 40 ml of dry dichloromethane and 1.4 ml of ethanethiol (1.18 g, 19 mmole) was cooled to −40° C. under nitrogen. Boron trifluoride etherate (1.0 ml) was then added. The solution was stirred at −40° C. under nitrogen. After 6 hours, the solution was quenched with a saturated sodium bicarbonate solution at −40° C., warmed up to room temperature, diluted with chloroform, washed with water, dried over anhydrous $Na_2SO_4$ and evaporated in vacuo to give a foam (1.4 g). This was dissolved in chloroform and chromatographed on four precoated silica gel TLC plates (E. Merck, 20 cm×20 cm×2 mm, 1:4 ethyl acetate-chloroform for development) and the bands were extracted with chloroform-methanol (8:2) to give in the order of increasing polarity, (11β)-17-(ethylthio)-17-[[(ethylthio)methyl]thio]-9-fluorohydroxyandrosta-1,4-dien-3-one (isomer A, 550 mg), the starting steroid (550 mg), and (11β)-17-[[(acetyloxy)methyl]thio]-9-fluorohydroxyandrosta-1,4-dien-3-one (isomer A, 250 mg). Another run on the same scale gave about the same results.

The 17-[[(acetyloxy)methyl]thio]-17-(ethylthio) product from both experiments was combined and recrystallized from acetone-hexane to give 400 mg of the product as an analytical specimen, melting point 190°–192° C., with consistent spectral data.

Anal. Calc'd. for $C_{24}H_{35}FO_4S_2$: C, 61.41; H, 7.10; F, 4.05; S, 13.68. Found: C, 61.31; H, 6.98; F, 3.92; S, 13.64.

The 17-(ethylthio)-17-[[(ethylthio)methyl]thio] product from both experiments was combined (1.1 g) and recrystallized from acetone-hexane to give 850 mg of the product as an analytical specimen, melting point 209°–212° C., with consistent spectral data.

Anal. Calc'd. for $C_{24}H_{35}FO_2S_3$: C, 61.23; H, 7.49; F, 4.06; S, 20.46. Found: C, 61.06; H, 7.55; F, 4.04; S, 20.31.

EXAMPLE 2

(11β)-2,2'-[(9-Fluoro-11-hydroxy-3-oxoandrosta-1,4-dien-17,17-diyl)bis(thio)]bisacetic acid, diethyl ester To a solution of 9-fluoro-11β-hydroxyandrosta-1,4-diene-3,17-dione (5.0 g, 16.0 mmole) in glacial acetic acid (100 ml) was added ethylthioglycolate (10.8 g, 90 mmole) and boron-trifluoride etherate (6.0 ml). After 1.0 hour the reaction mixture was diluted with water (500 ml) and extracted with chloroform. The chloroform extracts were combined, washed with a dilute sodium bicarbonate solution and water, dried (MgSO$_4$ anhydrous) and was evaporated in vacuo to afford the crude product as a syrup. This was chromatographed on a column of silica gel (60–200 mesh, 75 g) eluting the column successively with chloroform-hexane (8:2), chloroform and chloroform-ethyl acetate (95:5, 9:1 and 8:2) to isolate over-reacted steroid (~300 mg), the title compound (6.48 g) and unreacted starting steroid (800 mg). The 6.48 gram material was crystallized from methanol-water to afford the analytical specimen (5.3 g) melting point 125°–127° C., with consistent spectral data.

Anal. Calc'd for $C_{27}H_{37}FO_6S_2$: C, 59.97; H, 6.89; F, 3.51; S, 11.86. Found: C, 59.69; H, 6.75; F, 3.50; S, 11.82.

EXAMPLE 3

(11β,17α)-[[9-Fluoro-11-hydroxy-17-(methylthio)-3-oxoandrosta-1,4-dien-17-yl]thio]acetic acid, ethyl ester (A)

(11β)-[(9-Fluoro-11-hydroxy-3-oxoandrosta-1,4,16-trien-17-yl)thio]acetic acid, ethyl ester A solution of (11β)-2,2'-[(9-fluoro-11-hydroxy-3-oxoandrosta-1,4-dien-17,17-diyl)bis(thio)]bisacetic acid, diethyl ester (6.48 g; see example 2) in dry diethylbenzene (200 ml) was refluxed in contact with air for 4.0 hours. The solution was then cooled, diluted with some chloroform and was poured on a column of silica gel (60 g), eluting the column successively with chloroform and chloroform-ethyl acetate (95:5, 9:1 and 4:1) to isolate the title compound (4.15 g). One crystallization of this from ethyl acetate-hexane gave the analytical specimen of the title compound (3.8 g), melting point 144°–145° C., with consistent spectral data.

Anal. Calc'd for $C_{23}H_{29}FO_4S$: C, 65.68; H, 6.95; F, 4.52; S, 7.61. Found: C, 65.56; H, 6.87; F, 4.49; S, 7.52.

(B)

(11β,17α)-[[9-Fluoro-11-hydroxy-17-(methylthio)-3-oxoandrosta-1,4-dien-17-yl]thio]acetic acid, ethyl ester A solution of 1.0 g (2.38 mmole) of (11β)-[(9-fluoro-11-hydroxy-3-oxoandrosta-1,4,16-trien-17-yl)thio]acetic acid, ethyl ester in 50 ml of dry dichloromethane and 400 mg of methyl mercaptan was cooled to about −40° C. (acetonitrile-dry ice bath) under nitrogen. Boron trifluoride etherate (0.7 ml) was then added. The solution was stirred at approximately −40° C. under nitrogen for 3 hours, quenched with 10% sodium carbonate solution at the low temperature under vigorous stirring, diluted with chloroform, washed with water, dried over anhydrous Na$_2$SO$_4$ and evaporated in vacuo to give a foam (1.0 g.). This was dissolved in chloroform-hexane (4:1) and chromatographed on a 25-gram silica gel column, eluting successively with chloroform-hexane (4:1), chloroform and chloroform-ethyl acetate (95:5) to give 900 mg of the title compound. Recrystallization from acetone-hexane gave 770 mg of an analytical specimen, melting point 181°–182° C., with consistent spectral data.

Anal. Calc'd for $C_{24}H_{33}FO_4S_2$: C, 61.51; H, 7.10; F, 4.05; S, 13.68. Found: C, 61.38; H, 6.98; F, 4.24; S, 13.66.

EXAMPLE 4

(11β,17β)-[[9-Fluoro-11-hydroxy-17-(methylthio)-3-oxoandrosta-1,4-dien-17-yl]thio]acetic acid, ethyl ether A suspension of 9-fluoro-11β-hydroxy-17-(methylthio)androsta-1,4,16-trien-3-one (1.05 g) in dry dichloromethane (50 ml) containing ethyl mercaptoacetate (1.30 ml) was cooled and stirred under an atmosphere of nitrogen in a dry ice-acetonitrile bath (−40° to −45° C.) and boron trifluoride etherate (1.0 ml) was added. After 2.0 hours at about −40° C., the reaction was quenched under vigorous stirring by the addition of a 10% sodium carbonate solution (25 ml). The mixture was then warmed to room temperature, diluted with water and was extracted with chloroform. The chloroform solution was washed with water, dried (MgSO$_4$ anhydrous), evaporated, and the residue was absorbed on a column of silica gel (15 g). Successive elutions of the column with chloroform and ethyl acetate-chloroform (5:95 and 1:4) afforded in the later fractions the title compound as a solid (1.30 g). Crystallization of this from ethyl acetate-hexane followed by drying (70° C., 0.3 mm of Hg, 6.0 hours) gave the analytical specimen (1.10 g), melting point 168°–169° C., with consistent spectral data.

Anal. Calc'd for $C_{24}H_{33}FO_4S_2$: C, 61.51; H, 7.10; F, 4.05; S, 13.68. Found: C, 61.40; H, 7.19; F, 4.25; S, 13.85.

EXAMPLE 5

(11β,17β)-[[17-(Ethylthio)-9-fluoro-11β-hydroxy-3-oxoandrosta-1,4-dien-17-yl]thio]acetic acid, ethyl ester A suspension of 1.086 g (3 mmole) of 17-(ethylthio)-9-fluoro-11β-hydroxyandrosta-1,14,16-trien-3-one in 20 ml of dry dichloromethane and 1.32 g (12 mmole) of ethyl mercaptoacetate was cooled to about −40° C. (acetonitrile-Dry Ice bath) under nitrogen. Boron trifluoride etherate (0.75 ml, 6.1 mmole) was then added. The suspension gradually became a homogeneous solution. The solution was stirred at approximately −40° C. under nitrogen for 3 hours, quenched with saturated sodium bicarbonate solution at −40° C. under vigorous stirring, diluted with chloroform, washed with water, dried over anhydrous Na$_2$SO$_4$ and evaporated in vacuo to give a solid (1.4 g). This was redissolved in chloroform and chromatographed on a 30-gram silica gel column, eluting successively with chloroform and 95:5 chloroform-ethyl acetate to give 1.15 g of the title compound. Crystallization from acetone-hexane gave 835 mg of an analytical specimen, melting point 193°–194° C., with consistent spectral data.

Anal. Calc'd for $C_{25}H_{35}FO_4S_2$: C, 62.21; H, 7.31; F, 3.94; S, 13.29. Found: C, 62.32; H, 7.32; F, 3.77; S, 13.32.

EXAMPLE 6

(11β)-2,2'-[(9-Fluoro-11-hydroxy-3-oxoandrosta-1,4-dien-17,17-diyl)bis(thio)]bisacetic acid, dibutyl ester (A)

(11β)-2,2'-[(9-Fluoro-11-hydroxy-3-oxoandrosta-1,4-dien-17,17-diyl)bis(thio)]bisacetic acid, dibutyl ester To a solution of 9-fluoro-11β-hydroxyandrosta-1,4-diene-3,17-dione (4.0 g, 12.6 mmole) in glacial acetic acid (70 ml) containing n-butylthioglycolate (6.18 g, 42 mmole) was added boron trifluoride etherate (2.0 ml). After 1.5 hours, the mixture was poured into water (500 ml) and was extracted with chloroform. The chloroform solution was washed with water, a dilute NaHCO$_3$ solution and water, dried (MgSO$_4$ anhydrous) and was evaporated to afford the crude product as a glass. This was chromatographed on a column of silica gel (35 g) eluting the column successively with chloroform-hexane (4:1), chloroform and chloroform-ethyl acetate (9:1) to yield the title compound (4.90 g). A 1.2 g portion was repurified by preparative tlc on four Merck 2.0 mm preparative tlc plates using chloroform-ethyl acetate (7:3) for development and chloroform-ethanol (9:1) for extraction of the major band to isolate the homogeneous (tlc) title compound as a glass (1.0 g). This material resisted crystallization from the following solvent mixtures: methanol-water, ethanol-water, acetone-hexane, ethyl acetate-hexane and benzene-hexane. It was dried (70° C., 20 hours, 0.3 mm of Hg) to give the analytical specimen with consistent spectral data.

EXAMPLE 7

(11β,17β)-[[9-Fluoro-11-hydroxy-17-(methylthio)-3-oxoandrosta-1,4-dien-17-yl]thio]acetic acid (A)

(11β,17β)-[[11-Acetyloxy-9-fluoro-17-(methylthio)-3-oxandrosta-1,4-dien-17-yl]thio]acetic acid, ethyl ester A solution of 11β-acetyloxy-9-fluoro-17-(methylthio)androsta-1,4,16-triene-3-one (0.91 g) in dichloromethane (20 ml) containing ethyl mercaptoacetate (1.2 ml) was cooled and stirred in a dry ice-acetonitrile bath (about −45° C.) and boron trifluoride etherate (0.9 ml) was added. After 2.0 hours the reaction was quenched by the addition of a saturated sodium bicarbonate solution at the low temperature. The product was then isolated by extraction with chloroform. The crude product was chromatographed on a column of silica gel eluting successively with chloroform-hexane (1:1) and chloroform to afford the title compound as a solid (1.10 g), melting point 149°–151° C., with consistent spectral data.

(B)

(11β,17β)-[[9-Fluoro-11-hydroxy-17-(methylthio)-3-oxoandrosta-1,4-dien-17-yl]thio]acetic acid A solution of (11β,17β)-[[11-acetyloxy-9-fluoro-17-(methylthio)-3-oxoandrosta-1,4-dien-17-yl]thio]acetic acid, ethyl ester (1.0 g) in a mixture of ethanol (10 ml) and tetrahydrofuran (20 ml) was stirred under nitrogen and 3 M sodium hydroxide (3.0 ml) was added. After 2.0 hours, a moderate excess of acetic acid was added and the mixture was concentrated in vacuo. The concentrate was diluted with 5% HCl (100 ml) and was cooled in an ice bath. The steroid that separated was isolated by filtration, washed with water and was dried to afford a solid (0.805 g). Crystallization of this from acetone-hexane followed by drying (80° C., 0.3 mm of Hg, 6.0 hours) afforded the analytical specimen (650 mg) with consistent spectral data, melting point 229°–230° C., dec.

Anal. Calc'd. for C$_{22}$H$_{29}$FO$_4$S$_2$: C, 59.98; H, 6.63; F, 4.31; S, 14.55. Found: C, 59.70; H, 6.42; F, 4.14; S, 14.47.

EXAMPLE 8

(11β,17α)-9-Fluoro-11-hydroxy-17-(methylthio)-17-[[(methylthio)methyl]thio]androsta-1,4-dien-3-one and (11β,17β)-17-[[(acetyloxy)methyl]thio]-9-fluoro-11-hydroxy-17-(methylthio)androsta-1,4-dien-3-one A solution of 1.63 g (4.0 mmole) of 17-[[(acetyloxy)methyl]thio]-9-fluoro-11β-hydroxyandrosta-1,4,16-trien-3-one, 30 ml of dry dichloromethane and 1.3 g (27.1 mmole) of methyl mercaptan was cooled to −40° C. (acetonitrile-Dry Ice bath) under nitrogen. Boron trifluoride etherate (1.0 ml) was then added. The solution was stirred at −40° C. under nitrogen for 4.5 hours, quenched with a saturated NaHCO$_3$ solution (saturated with CO$_2$) at low temperature, diluted with chloroform, washed with water, dried over anhydrous Na$_2$SO$_4$ and evaporated in vacuo to give an amorphous solid (1.7 g). Another run using 1.22 g (3.0 mmole) of the starting steriod gave 1.3 g of amorphous solid identical in tlc to the 1.7 g material. These two were combined, dissolved in chloroform and chromatographed on 8 precoated silica gel TLC plates (E. Merck, 20 cm×20 cm×2 mm, 1:4 ethyl acetate-chloroform for development) to give in order of increasing polarity the following homogeneous (tlc) solids: 680 mg of the 17-(methylthio)-17-[[(methylthio)methyl]thio], product, 800 mg of the starting steriod and 1.2 g of the 17-[[(acetyloxy)methyl]thio]-17-(methylthio) product.

The 17-(methylthio)-17-[[(methylthio)methyl]thio]-product was recrystallized from methanolchloroform to give 450 mg of an analytical specimen, melting point 215°–217° C., dec., with consistent spectral data.

Anal. Calc'd. for C$_{22}$H$_{31}$FO$_2$S$_3$: C, 59.69; H, 7.06; F, 4.29; S, 21.73. Found: C, 59.95; H, 7.09; F, 4.16; S, 21.54.

The 17-[[(acetyloxy)methyl]thio]-17-(methylthio) product was recrystallized from acetone-hexane to give 800 mg of an analytical specimen, melting point 220°–221° C., with consistent spectral data. [On the basis of NMR, it seemed that about 10% of the 17-stereoisomer was also present. The IR spectrum in KBr showed two carbonyl absorptions for the acetate while in chloroform solution only one peak was observed.]

Anal. Calc'd for C$_{23}$H$_{31}$FO$_4$S$_2$: C, 60.76; H, 6.87; F, 4.18; S, 14.11. Found: C, 60.66; H, 6.74; F, 3.91; S, 14.01.

EXAMPLE 9

(11β,17β)-9-Fluoro-11-hydroxy-17-(methylthio)-17-[(phenylmethyl)thio]androsta-1,4-dien-3-one (A)

(11β,17β)-11-(Acetyloxy)-9-fluoro-17-(methylthio)-17-[(phenylmethyl)thio]androsta-1,4-dien-3-one To a magnetically stirred solution of 11β-(acetyloxy)-9-fluoro-17-(methylthio)androsta-1,4,16-trien-3-one (1.13 g, 3.0 mmole) in 45.0 ml of distilled dichloromethane maintained at −78° C. (Dry Ice/acetone bath) under a nitrogen atmosphere was added benzyl mercaptan (1.4 ml, 12.0 mmole) followed by boron trifluoride etherate (1.5 ml, 12.0 mmole). After 27.5 hours, the reaction mixture was quenched at 0° C. with water and allowed to warm to room temperature before it was chloroform extracted (three 200 ml portions). The collected chloroform layers were washed with a saturated Na$_2$CO$_3$ solution, separated, dried over anhydrous MgSO$_4$ and then rotary evaporated to a crystalline solid. The solid was dried on a steam bath (vacuum pump, 2.0 hours) to yield 0.91 g.

(B)

(11β,17β)-9-Fluoro-11-hydroxy-17-(methylthio)-17-[(phenylmethyl)thio]androsta-1,4-dien-3-one To a magnetically stirred solution of (11β,17β)-11-(acetyloxy)-9-fluoro-17-(methylthio)-17-[(phenylmethyl)thio]androsta-1,4-dien-3-one (0.91 g) in methanol (24.0 ml), tetrahydrofuran (48.0 ml), and water (6.0 ml) under a nitrogen atmosphere was injected a 12% sodium hydroxide solution (3.0 ml) which resulted in a brownish color. After a total of 100 minutes the mixture was chloroform extracted, washed with water, dried over anhydrous MgSO$_4$ and rotary evaporated to an oil. This was dissolved in 25.0 ml of hot ethyl acetate and left to crystallize in the freezer overnight. This crystallization yielded 0.426 g of an analytical specimen, melting point 244°–245° C., with consistent spectral data.

Anal. Calc'd for $C_{27}H_{34}O_2S_2F_1$: C, 68.46; H, 7.23; F, 4.01; S, 13.54. Found: C, 68.57; H, 6.92; F, 4.07; S, 13.30.

EXAMPLE 10

(11β)-9-Fluoro-11-hydroxy-17,17-bis[(phenylmethyl)thio]androsta-1,4-dien-3-one

To a magnetically stirred solution of 9-fluoro-11β-hydroxyanydrosta-1,4-dien-3,17-dione (642 mg) in 7.0 ml of glacial acetic acid and 3.0 ml of dry dichloromethane under nitrogen at 0° C. was added 1.4 ml of benzyl mercaptan followed by 0.49 ml of boron trifluoride etherate. The reaction mixture turned dark brown with time and after 25.0 minutes, at 0° C., it was quenched with a saturated sodium carbonate solution. The mixture was then extracted with chloroform (three 150 ml portions) and the collected chloroform extracts were washed with water, dried over anhydrous MgSO$_4$, and rotary evaporated to a solid residue. The residue was preadsorbed on Baker silica gel (dissolved in 20% hexane:80% chloroform) and flash chromatographed. The desired product was successfully eluted using a 4% ethyl acetate:96% chloroform as the mobile phase. Product containing fractions were pooled and rotary evaporated to give the title compound (350 ml) which was recrystallized from ethyl acetate to yield the analytical specimen (280 mg), with consistent spectral data.

Anal. Calc'd for $C_{33}H_{39}O_2S_2F$: C, 71.97; H, 7.14; S, 11.64; F, 3.45. Found: C, 72.09; H, 6.76; S, 11.56; F, 3.39.

What is claimed is:

1. A steriod having the formula

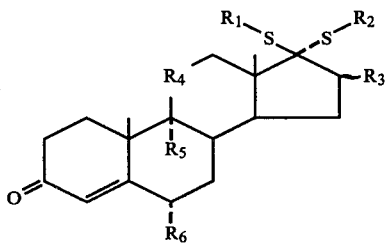

or 1,2-, 6,7- and 15,16-dehydro derivatives thereof, wherein
one of $R_1$ and $R_2$ is alkyl, cycloalkyl, aryl, arylalkyl, or —CH$_2$X wherein X is alkylthio, alkoxy, alkanoyloxy, aroyloxy or alkoxycarbonyl, and the other is alkylthioalkyl, alkoxyalkyl, alkanoyloxyalkyl, aroyloxyalkyl, alkoxycarbonylalkyl, carbonyalkyl or arylalkyl;
$R_3$ is hydrogen, hydroxy, alkoxy, aryloxy, oxo, methylene, alkylthio, arylthio, alkanoyl, alkanoyloxy, or halogen;
$R_4$ is carbonyl or β-hydroxymethylene;
$R_5$ is hydrogen or halogen; and
$R_6$ is hydrogen, methyl, hydroxy, alkanoyl or halogen.

2. A steroid in accordance with claim 1 wherein $R_3$ is hydrogen.

3. A steroid in accordance with claim 1 wherein $R_4$ is β-hydroxymethylene.

4. A steroid in accordance with claim 1 wherein $R_5$ is fluorine.

5. A steroid in accordance with claim 1 wherein $R_6$ is hydrogen.

6. A steroid in accordance with claim 1 wherein $R_3$ is hydrogen, $R_4$ is β-hydroxymethylene, $R_5$ is fluorine and $R_6$ is hydrogen.

7. The compound in accordance with claim 1 (11β)-17-[[(acetyloxy)methyl]thio]-17-(ethylthio)-9-fluoro-11-hydroxypregna-1,4-dien-3-one or (11β)-17-(ethylthio)-17-[[(ethylthio)methyl]thio]-9-fluoro-hydroxyandrosta-1,4-dien-3-one.

8. The compound in accordance with claim 1 (11β)-2,2'-[(9-fluoro-11-hydroxy-3-oxoandrosta-1,4-dien-17,17-diyl)bis(thio)]bisacetic acid, diethyl ester.

9. The compound in accordance with claim 1 (11β,17α)-[[9-fluoro-11-hydroxy-17-(methylthio)-3-oxoandrosta-1,4-dien-17-yl]thio]acetic acid, ethyl ester.

10. The compound in accordance with claim 1 (11β,17β)-[[9-fluoro-11-hydroxy-17-(methylthio)-3-oxoandrosta-1,4-dien-17-yl]thio]acetic acid, ethyl ester.

11. The compound in accordance with claim 1 (11β,17β)-[[17-(ethylthio)-9-fluoro-11β-hydroxy-3-oxoandrosta-1,4-dien-17-yl]thio]acetic acid, ethyl ester.

12. The compound in accordance with claim 1 (11β)-2,2'-[(9-fluoro-11-hydroxy-3-oxoandrosta-1,4-dien-17,17-diyl)bis(thio)]bisacetic acid, dibutyl ester.

13. The compound in accordance with claim 1 (11β,17β)-[[9-fluoro-11-hydroxy-17-(methylthio)-3-oxoandrosta-1,4-dien-17-yl]thio]acetic acid.

14. The compound in accordance with claim 1 (11β,17α)-9-fluoro-11-hydroxy-17-(methylthio)-17-[[(methylthio)methyl]thio]androsta-1,4-dien-3-one or (11β,17β)-17-[[(acetyloxy)methyl]thio]-9-fluoro-11-hydroxy-17-(methylthio)androsta-1,4-dien-3-one.

15. The compound in accordance with claim 1 (11β,17β)-9-fluoro-11-hydroxy-17-(methylthio)-17-[(phenylmethyl)thio]androsta-1,4-dien-3-one.

16. The compound in accordance with claim 1 (11β)-9-fluoro-11-hydroxy-17,17-bis[(phenylmethyl)thio]androsta-1,4-dien-3-one.

* * * * *

UNITED STATES PATENT AND TRADEMARK OFFICE
CERTIFICATE OF CORRECTION

PATENT NO. : 4,447,363
DATED : May 8, 1984
INVENTOR(S) : Ravi K. Varma

It is certified that error appears in the above-identified patent and that said Letters Patent is hereby corrected as shown below:

The structural formula VI should read as follows:

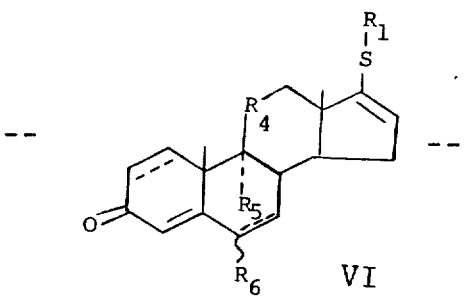

The structural formula XII should read as follows:

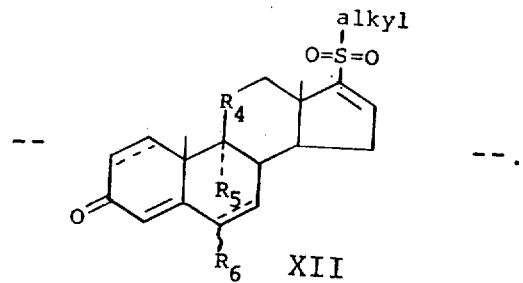

UNITED STATES PATENT AND TRADEMARK OFFICE
CERTIFICATE OF CORRECTION

PATENT NO. : 4,447,363
DATED : May 8, 1984
INVENTOR(S) : Ravi K. Varma

It is certified that error appears in the above—identified patent and that said Letters Patent is hereby corrected as shown below:

The title of Example 1 should read --(11β)-17-[[(Acetyloxy)methyl]thio]-17-(ethylthio)-9-fluoro-11-hydroxypregna-1,4-dien-3-one (isomer A)--.

In column 11, line 44, "(350 ml)" should read --(350 mg)--.

Signed and Sealed this

Twelfth Day of February 1985

[SEAL]

*Attest:*

DONALD J. QUIGG

*Attesting Officer*   *Acting Commissioner of Patents and Trademarks*